(12) United States Patent
Olander et al.

(10) Patent No.: US 6,783,962 B1
(45) Date of Patent: Aug. 31, 2004

(54) PARTICULATE MATERIAL FOR PURIFICATION OF BIO-MACROMOLECULES

(75) Inventors: Morten Aae Olander, Copenhagen (DK); Allan Otto Fog Lihme, Birkerød (DK); Timothy John Hobley, Copenhagen (DK); Marcos Simon, Copenhagen (DK); Irini Theodossiou, Copenhagen (DK); Owen Robert Tyrynis Thomas, Copenhagen (DK)

(73) Assignee: UpFront Chromatography, Copenhagen (DK)

( * ) Notice: Subject to any disclaimer, the term of this patent is extended or adjusted under 35 U.S.C. 154(b) by 0 days.

(21) Appl. No.: 09/936,925

(22) PCT Filed: Mar. 24, 2000

(86) PCT No.: PCT/DK00/00142

§ 371 (c)(1),
(2), (4) Date: Nov. 20, 2001

(87) PCT Pub. No.: WO00/57982

PCT Pub. Date: Oct. 5, 2000

(30) Foreign Application Priority Data

Mar. 26, 1999 (DE) .......................... 1999 00415

(51) Int. Cl.⁷ .................. C12P 19/34; C12N 11/10; G01N 33/548; C07K 1/00; C07K 17/10
(52) U.S. Cl. .................. 435/91.1; 435/176; 435/178; 435/180; 435/803; 435/815; 436/524; 436/529; 436/531; 530/412; 530/413; 530/415; 530/811; 530/813; 530/815; 536/22.1
(58) Field of Search .............. 435/91.1, 174, 435/176, 178, 180, 815, 803; 436/529, 524, 531; 530/402, 412, 413, 415, 813, 811, 815; 536/22.1

(56) References Cited

U.S. PATENT DOCUMENTS 5,770,416 A * 6/1998 Lihme et al. ............... 435/176
5,780,593 A * 7/1998 Lihme et al. ............... 530/361
5,866,006 A * 2/1999 Lihme et al. ............... 210/635

FOREIGN PATENT DOCUMENTS

| DK | 280430926 A1 | 10/1977 |
| EP | 0 607 998 A2 | 7/1994 |
| EP | 0 538 350 B1 | 9/1996 |
| WO | WO 86/03136 | 6/1986 |
| WO | WO 92/00799 | 1/1992 |
| WO | WO 92/18237 | 10/1992 |
| WO | WO 97/17132 | 5/1997 |
| WO | WO 97/291 | 8/1997 |

OTHER PUBLICATIONS

Prazeres, et al.; "Preparative purification of . . . ", Journal of Chromatography A. 806 (1998) 31–45.

Braas, Genevieve et al.; "Strategies for the Isolation . . . ", Bioseparaium 6:211–228, 1996.

Lyddiatt, Andrew et al.; "Biochemical recovery . . . " Current Opinion in Biotechnology 1998, 9:177–185.

* cited by examiner

*Primary Examiner*—David M. Naff
(74) *Attorney, Agent, or Firm*—Birch, Stewart, Kolasch & Birch, LLP

(57) ABSTRACT

The present invention relates to particulate material having a density of at least 2.5 g/ml, where the particles of the particulate material have an average diameter of 5–75 μm, and the particles of the particulate material are essentially constructed of a polymeric base matrix, e.g. a polysaccharide such as agarose, and a non-porous core material, e.g. steel and titanium, said core material having a density of at least 3.0 g/ml, said polymeric base matrix including pendant groups which are positively charged at pH 4.0 or which are affinity ligands for a bio-molecule. Possible pendant groups include polyethyleneimine (PEI), diethylaminoethyl (DEAE) and quaternary aminoethyl (QAE). The materials are useful in expanded bed or fluidized bed chromatography processes, in particular for purification of bio-macromolecules such as plasmid DNA, chromosomal DNA, RNA, viral DNA, bacteria and viruses.

32 Claims, 5 Drawing Sheets

PARTICULATE MATERIAL FOR PURIFICATION OF BIO-MACROMOLECULES

FIELD OF THE INVENTION

Figure 1:
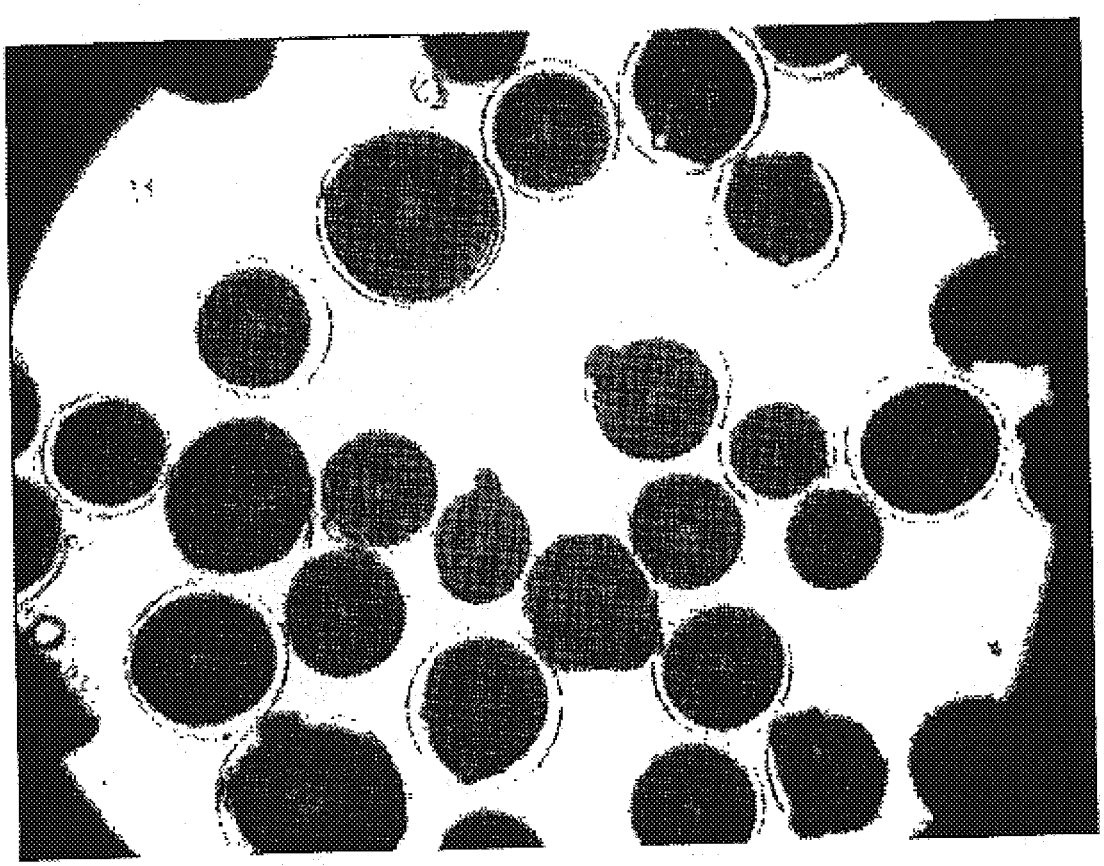

A fluidised/expanded bed adsorption process for purification of bio-macromolecules is described. The method has been developed to be a first capture step in a downstream process in the production of bio-macromolecules such as nucleic acids, e.g. plasmid DNA, chromosomal DNA, RNA and virus DNA, and viruses themselves, and even bacteria.

BACKGROUND OF THE INVENTION

With the growing interest in gene therapy, the need to produce large quantities of gene therapy vectors becomes more pressing. Currently 24% of protocols under trial employ plasmid DNA as the delivery vehicle for gene therapy and vaccine applications. Viral DNA is also used as delivery vehicle in many gene therapy cases. Given the large size of gene vector molecules and the shear sensitivity of the solids produced following cell lysis and neutralisation to extract the gene vectors from microbial cells or viral material, traditional unit operations such as centrifugation, filtration and packed bed chromatography are not especially attractive. Fluidised bed adsorption or expanded bed adsorption, techniques based on fluidisation, offer considerable promise with intractable biological feedstock containing insoluble impurities.

An expanded bed is characterised by low degree of back-mixing of the adsorbent media. This means that each adsorbent particle move within a limited volume of the total bed. An expanded bed is called a stabilised fluidised bed. The stability occur when the adsorbent particles make up a so called classified bed where the larger and/or most dense adsorbent particles are positioned furthest down in the bed and the smaller and/or less dense adsorbent particles are positioned further up in the bed. The adsorbent media used in this invention is designed for use in a fluidised and preferable in an expanded bed. The size distribution and density variation determine the stability of the bed. As used herein, the term "fluidised/expanded" bed refers to that the unit operation at least is a fluidised bed and preferable an expanded bed.

There are at present at least two commercial suppliers of adsorbents for expanded bed chromatography. Pharmacia Biotech AB (Uppsala, Sweden) market Streamline™ (which utilises adsorbents of cross-linked polysaccharides (agarose) with quartz particles incorporated as high density fillers. The adsorbents have a density of about 1.2 g/ml with diameters being in the range of 125–315 µm. WO92/18237 (Pharmacia LKB Biotechnology AB) describe beads for down stream processing comprising a polymer matrix into which glass or silica particles have been incorporated, and their use in down stream processing, especially stabilised fluidised bed separations. The beads have a diameter of 100–1000 µm and a density of 1.10–1.50 g/ml of hydrated beads. The core materials are typically glass or silica.

WO 92/00799 (Kem-En-Tec, UpFront Chromatography A/S) describe adsorbent particles having a structure that is characterised by being pellicular or a conglomerate. This publication discloses a large number of adsorbents for use in fluidised/expanded bed chromatography.

WO 97/17132 (Pharmacia Biotech AB (Uppsala, Sweden) describes adsorbents for use in expanded bed chromatography, that is characterised by having a density of more than 1 g/ml and comprising a porous polymer base matrix in which a particulate filler is incorporated. The filler is characterised by having a density $\geq 3$ g/ml, but the size of the core material particles "will always be much smaller than the size of the beads". Thus, the density of the beads are normally just above 1.0 g/cm$^3$.

Also described in the literature (oral presentation by E. Boschetti, BioSepra, on Second International Conference on Expanded Bed Adsorption, Napa Valley; Calif., USA, 21–23 June, 1998, see conference abstract book, page 14) is the use of small, high density particles suitable for fluid bed applications. The adsorbents described are designed to reduce the diffusion distance in a porous media inside the adsorbents. The adsorbents described are favourable to rapid diffusion and therefore compatible with high flow rates.

The adsorbent media commercially available today for fluidised/expanded bed chromatography has mainly been developed for protein purification. A fraction of the media has a high density (>1 g/ml) to ensure the sedimentation properties needed. The high density fraction is ideally inert and non corrosive under the conditions used during the particular purification. The high density fraction is combined with a polymer phase with an open pore structure where the target molecule (usually a protein) of interest can bind to a ligand coupled to the polymer. The target molecule is able to diffuse into the pores.

Thereby, the target molecule is exposed to binding sites in the whole volume of the polymer phase. The target bio-macromolecules described in the method here, e.g. plasmid DNA, chromosomal DNA, RNA, virus DNA and viruses themselves, and even bacteria are not able to diffuse into the pores of the commercially available media designed for expanded bed chromatography. Therefore is the binding likely to occur mainly to the surface of the media. With the media available today this constitute an important limitation of capacity, because of their relatively low available surface ares.

WO 97/29190 describes a technique for production of highly purified plasmid DNA in E. coli, which method includes growing plasmid containing cells to a high biomass in exponential growth, and lysing the cells by raising the pH of the culture to a carefully controlled pH value in which chromosomal DNA is denatured, but plasmid DNA is reversibly renatured. The plasmid containing feedstock is subsequently processed on a diethylaminoethyl (DEAE) anion exchanger in an expanded bed process.

Journal of Chromatography A, 806 (1998) 31–45 describes preparative purification of super-coiled plasmid DNA using quaternary amino ethyl (QAE) anion exchange chromatography.

BRIEF DESCRIPTION OF THE INVENTION

Thus the problem behind the present invention is to provide improved materials for fluidised bed adsoption or expanded bed adsorption, in particular materials for the purification of bio-macromolecules.

The present invention, thus, provides a method for the use of fluidised bed adsorption or expanded bed adsorption as a first capture step for recovery of bio-macromolecules, e.g. plasmid DNA, chromosomal DNA, RNA, viral DNA and viruses themselves, and even bacteria, from crude biologically feedstock, e.g. recovery of plasmid DNA from an E. coli, lysate feedstock. Novel particulate materials are also described.

A first objective is to provide a particulate material (an adsorbent media) that have an improved binding capacity for bio-macromolecules, e.g. plasmid DNA, chromosomal DNA, RNA, virus DNA, viruses as such and bacteria, through a hitherto unrealised combination of particle size, particle density and pendant groups (ligands) thereby offering certain advantages in chromatographic processes such as fluid bed processes. Thus, the present invention also provides a particulate material having a density of at least 2.5 g/ml, where the particles of the particulate material have an average diameter of 5–75 µm, and the particles of the particulate material are essentially constructed of a polymeric base matrix and a non-porous core material, said core material having a density of at least 3.0 g/ml, said polymeric base matrix including pendant groups which are positively charged such as at pH 4.0 or pH 6.0 or which are affinity ligands for a bio-molecule.

A second objective of the invention is to provide a method that can handle large scale production of bio-macromolecules, e.g. plasmid DNA, chromosomal DNA, RNA, virus DNA and viruses themselves, and even bacteria from crude feedstock using fluidised/expanded bed adsorption as a first capture step. Thus, the present invention provides a method for the isolation or purification of a bio-macromolecule, wherein said bio-macromolecule is adsorbed to a particulate material as defined in any of the claims 1–15.

Application of the materials is generally envisaged to be carried out in non-packed systems such as non-packed columns or non-packed reactors and contactors of different kinds.

It is especially envisaged that the materials can be used within the fields of expanded bed processes and fluidised bed processes as well as within processes relating to turbulent fluid beds, batch adsorption and batch elution and batch adsorption followed by expanded bed elution. As will be understood, the materials can be used in quite a wide range of chromatographic processes, however it should be mentioned that the present materials are not intended for packed bed applications.

DETAILED DESCRIPTION OF THE INVENTION

The present inventors have discovered a method that gives high dynamic capacity in capture of bio-macromolecules in fluidised/expanded bed adsorption. The method is able to handle large volumes of crude feedstock containing the target bio-macromolecule.

The term bio-macromolecule is intended to mean any entity of biological origin having a molecular weight of at least 20,000 D, e.g. plasmid DNA, chromosomal DNA, RNA, virus DNA or viruses themselves, and even bacteria. It should be understood that modified variants and analogues of these entities are also possible within the scope of the term as long as the modification or analogues maintain the character of the native bio-macromolecule. The bio-macromolecules to be isolated/purified according to the present invention preferably have a molecular weight of at least 50,000 D, such as at least 100,000 D or at least 500,000 D such as at least 5,000,000. As an example, in *E. coli* the molecular weight will typically be 4,200,000 base pairs corresponding $2.7 \times 10^9$ D. It will be appreciated that no definite upper limit for the molecular weight applies as the bio-macromolecules also include entire cells. However, with respect to nucleic acids, e.g. plasmid DNA, chromosomal DNA, RNA, virus DNA, etc. the "molecular diameter" is typically in the range of 0.5–5.0 µm. Viruses typically have a "diameter" in the range of 50–100 nm.

Particulate Material

As mentioned above, the present invention, i.a., relates to a particulate material useful for the isolation/purification of bio-macromolecules, i.e. a particulate material having a density of at least 2.5 g/ml, where the particles of the particulate material have an average diameter of 5–75 µm, and the particles of the particulate material are essentially constructed of a polymeric base matrix and a non-porous core material, said core material having a density of at least 3.0 g/ml, said polymeric base matrix including pendant groups which are positively charged at pH 4.0 or which are affinity ligands for a bio-molecule.

In the present context, the terms "adsorbents", "particulate material" and "adsorption media" are used synonymous.

In the present context the expression "conglomerate" is intended to designate a particle of a particulate material, which comprises beads of core material of different types and sizes, held together by the polymeric base matrix, e.g. a particle consisting of two or more high density particles held together by surrounding agarose (polymeric base matrix). The expression "pellicular" is intended to designate a composite of particles, wherein each particle consists of only one high density core material coated with a layer of the polymeric base matrix, e.g. a high density stainless steel bead coated with agarose (see FIG. 1).

It is believed that the relatively small diameter of the particles combined with the high density play an important role for the useful properties of the particulate material, in particular the useful properties in the isolation/purification of bio-macromolecules in fluidised bed processes. Thus, the average diameter of the particles of the particulate material is 5–75 µm, such as in the range of 10–60 µm, such as in the range of 12–49 µm, more preferable in the range of 20–40 µm.

Furthermore, it is believed that a relatively narrow particle size distribution is advantageous (bearing in mind that a certain breadth of the distribution is advantageous when the material is to be use in a fluidised bed set-up), thus, it is believed that at least 95% of the particles should have a diameter in the range of 5–80 µm, such as 15–45 µm, preferably in the range of 20–40 µm.

As mentioned above, the high density of the particles appears to be extremely relevant, thus, in general, the density should be at least 2.5, e.g. at least 3.0, such as at least 3.5, preferably in the range of 3.5–10.0 g/ml.

The high density is primarily obtained by inclusion of a high proportion of a dense non-porous core materials, preferably having a density of at least 3.0 g/ml, such as at least 5.0, preferably in the range of 6.0–12.0 g/ml. This will result in particles which are pellicular or a conglomerate in composition. Examples of suitable non-porous core materials are inorganic compounds, metals, elementary non-metals, metal oxides, non-metal oxides, metal salts and metal alloys, etc. as long as the density criteria above are fulfilled. Examples of such core materials are metal silicates metal borosilicates; ceramics including titanium diboride, titanium carbid, zirconium diboride, zirconium carbide, silicon carbide, aluminium nitride, silicon nitride, titanium nitride, yttrium oxide, silicon metal powder, and molybdenum disilide; metal oxides and sulphides, including magnesium, aluminium, titanium, vanadium, chromium, zirconium, hafnium, manganese, iron, cobalt, nickel, copper and silver oxide; non-metal oxides; metal salts, including barium sulphate; metallic elements, including zirconium, titanium, hafnium, vanadium, chromium, manganese, iron, cobalt, nickel, indium, copper, silver, gold, palladium, platinum, ruthenium, osmium, rhodium and iridium, and alloys of metallic elements, such as alloys formed between said metallic elements, e.g. stainless steel; crystalline and amorphous forms of carbon, including graphite, carbon black and charcoal. Preferred are steel and titanium beads such as stainless steel beads.

It is preferred that the core material of at least 95% of the particles is a steel bead having a diameter in the range of 2–40, such as 15–38 µm, preferably 15–35 µm.

Furthermore, it is preferred that at least 95% of the particles comprises one non-porous core material having a diameter which is at least 0.70, such as at least 0.80, preferably at least 0.85, of the diameter of the particle.

Alternatively, the core material is constituted by more than one bead, e.g. beads having a diameter of less that 20 µm.

Typically, the core material constitutes 10–99%, preferably 50–95%, of the volume of the particles, and the polymer base matrix constitutes 1–90%, preferably 5–50%, of the volume of the particle.

When the core material of a large proportion of the particles (>95%) is constituted by one bead, the polymeric base matrix is typically less than 50 µm in thickness (the geometrical distance between the core material and the surface of the particle) and preferable less than 20 µm, even more preferable less than 10 µm, and most preferable less than 5 µm in thickness. In one embodiment, it is envisaged that the polymeric base matrix may constitute a mono molecular layer covering the core material. Thus, in this instance, it is contemplated that the polymeric matrix may be replaced with low-molecular weight species having an predominant affinity for the core material. This affinity between the low-molecular species and the core material may be improved by surface treatment of the core material, e.g. by organosilylation of ceramic materials. The monomolecular layer may also be covalently coupled to the surface of the core material by chemical means known per se.

Another important feature of the present invention is the fact that the polymeric base matrix comprises either chargeable pendant groups or affinity ligands for a bio-macromolecule as pendant groups. It is also possible to combine the two sub-types of pendant groups. It is currently preferred that the pendant groups comprise chargeable moieties selected from polyethyleneimine, modified polyethyleneimine, poly(ethyleneimine/oxyethylene), quaternary aminoethyl (QAE) and diethylaminoethyl (DEAE). Such groups may be linked to the polymeric base matrix by means of a divinyl sulphone or a epichlorohydrin linker or by other means of linking known per se or by using the chloride corresponding to the group. The first-mentioned possibility is particularly relevant for chargeable moieties like polyethyleneimines, modified (e.g. alkylated) polyethyleneimines and poly(ethyleneimine/oxyethylene)s. The corresponding chloride is especially relevant for chargeable groups like quaternary aminoethyl (QAE) and diethylaminoethyl (DEAE).

For the binding of bio-macromolecules to the surface of the particulate material according to the invention, a large number of different ligands known per se may be employed by coupling to the polymer phase, directly or by the below-mentioned activating groups. Positively charged ion exchange ligands are well suited for the binding of nucleic acids such as DNA and RNA, well known ligands being DEAE, QAE, PEI, and other amino group containing ligands. However, also interchalating ligands may be employed as well as sequence specific ligands such as complementary DNA/RNA strands and artificial oligonucleotides such as PNA.

Polyclonal and monoclonal antibodies, synthetic peptides and other synthetic chemical oligomers, lectins, carbohydrates and hydrophobic ligands may also be relevant for the binding of virus, bacteria and other bio-macromolecules.

Such affinity ligands, like the chargeable moieties, may be linked to the base matrix by method known to the person skilled in the art, e.g. as described in "Immobilized Affinity Ligand Techniques" by Hermanson et al., Academic Press, Inc., San Diego, 1992. In cases where the polymeric base matrix do not have the properties to function as an active substance, the polymeric base matrix (or matrices where a mixture of polymers are used) may be derivatised to function as an active substances in the procedures of activation or derivatisation. Thus, materials comprising hydroxyl, amino, amide, carboxyl or thiol groups may be activated or derivatised using various activating chemicals, e.g. chemicals such as cyanogen bromide, divinyl sulfone, epichlorohydrin, bisepoxyranes, dibromopropanol, glutaric dialdehyde, carbodiimides, anhydrides, hydrazines, periodates, benzoquinones, triazines, tosylates, tresylates, and diazonium ions.

In a preferred embodiment, the pendant group is a polyethyleneimine chain, more preferably a polyethyleneimine chains having an weight average molecular weight of at least 10,000 D, such as 50,000–2,000,000 D.

It is also preferred, irrespective of whether the pendant group is a polyethyleneimine, that the pendant groups form a tentacular structure on the surface of the particle. A tentacular surface structure is preferred to increase the surface area and/or the binding sites for large bio-macromolecules themselves. It should be understood that moieties like polyethyleneimine may form a coiled structure which is believed to facilitate the adsorption of bio-macromolecules. Other ligands suitable for capture of bio-macromolecules such as plasmid DNA are the DEAE and QAE. They themselves do not construct a tentacular structure when coupled to an adsorbent media. In combination with spacers, ligands like DEAE and QAE can, however, form a tentacular structure with enhanced surface area. Also other low molecular weight ligand, e.g. oligonucleotides, can be useful, in particular in combination with a tentacular surface structure.

The polymeric base matrix is used as a means of covering and keeping multiple (or a single) core material together and as a means for binding the active substance. Thus, the polymeric base matrix is to be sought among certain types of natural or synthetic organic polymers, typically selected from A) natural and synthetic polysaccharides and other carbohydrate based polymers, including agar, alginate, carrageenan, guar gum, gum arabic, gum ghatti, gum tragacanth, karaya gum, locust bean gum, xanthan gum, agaroses, celluloses, pectins, mucins, dextrans, starches, heparins, chitosans, hydroxy starches, hydroxypropyl starches, carboxymethyl starches, hydroxyethyl celluloses, hydroxypropyl celluloses, and carboxymethyl celluloses.

B) synthetic organic polymers and monomers resulting in polymers, including acrylic polymers, polyamides, polyimides, polyesters, polyethers, polymeric vinyl compounds, polyalkenes, and substituted derivatives thereof, as well as copolymers comprising more than one such polymer functionally, and substituted derivatives thereof; and C) mixture thereof.

A preferred group of polymeric base matrices are polysaccharides such as agarose.

The ideal and preferred shape of a single particle is substantially spherical. The overall shape of the particles is, however, normally not extremely critical, thus, the particles can have other types of rounded shapes, e.g. ellipsoid, droplet and bean forms. However, for certain applications (e.g. when the particles are used in a fluidised bed set-up), it is preferred that at least 95% of the particles are substantially spherical.

In one preferred embodiment, the particulate material has a density of in the range of 3.2–5.0 g/ml, where the particles of the particulate material have an average diameter of 15–45 µm, and the particles of the particulate material are essentially constructed of a polysaccharide base matrix and a core material, said core material having a density in the range of 6.0–12.0 g/m$^3$, said polysaccharide base matrix including pendant chains of polyethyleneimine, modified polyethyleneimine or poly(ethyleneimine/oxyethylene), said pendant groups forming a tentacular structure on the surface of the particle.

In a further preferred embodiment, the present invention provides to a particulate material having a density of at least 2.5 g/ml, where the particles of the particulate material have an average diameter of 5–75 µm, and the particles of the particulate material are essentially constructed of a polymeric base matrix selected from polysaccharides, preferably agarose, and a non-porous core material, said core material having a density in the range of 6.0–12.0 g/ml where at least 95% of the particles comprises one non-porous core material bead having a diameter which is at least 0.70 of the diameter of the particle, said polymeric base matrix including pendant groups which are positively charged at pH 4.0 or which are affinity ligands for a bio-molecule.

Preparation of the particulate material according to the invention can be performed by various methods known per se (e.g. by conventional processes known for the person skilled in the art, see e.g. EP 0 538 350 B1 (UpFront Chromatography A/S) or WO 97/17132 (Pharmacia Biotech AB)), for example by block polymerisation of monomers; suspension polymerisation of monomers; block or suspension gelation of gel-forming materials, e.g. by heating and cooling (e.g. of agarose) or by addition of gelation "catalysts" (e.g. adding a suitable metal ion to alginates or carrageenans); block or suspension cross-linking of suitable soluble materials (e.g. cross-linking of dextrans, celluloses, or starches or gelatines, or other organic polymers with e.g. epichlorohydrin or divinyl sulphone); formation of silica polymers by acidification of silica solutions (e.g. block or suspension solutions); mixed procedures e.g. polymerisation and gelation; spraying procedures; and fluid bed coating of density controlling particles; cooling emulsions of density controlling particles suspended in polymeric base matrices in heated oil solvents; or by suspending density controlling particles and active substance in a suitable monomer or copolymer solution followed by polymerisation.

In a particular preferred embodiment (which appears to be generally applicable for the preparation of the particulate material according to the invention), a particulate material comprising agarose as the polymeric base matrix and steel beads as the core material is obtained by heating a mixture of agarose in water (to about 90° C.), adding the steel beads to the mixture and transferring the mixture to a hot oil (e.g. vegetable oils), emulsifying the mixture by vigorous stirring (optionally by adding a conventional emulsifier) and cooling the mixture. It will be appreciated by the person skilled in the art, that the particle size (i.e. the amount of polymeric base matrix (here: agarose) which is incorporated in each particle can be adjusted by varying the speed of the mixer and the cooling process.

As will be apparent from the following, the particulate material is highly useful for use in any chromatographic processes, in particular in fluidised bed adsorption processes.

The Method

A column designed for fluidised/expanded bed chromatography is used for the process, e.g. a column with a distribution plate in the inlet, or a column where the raw material is distributed properly in a local mixing zone in the bed by a mechanical stirrer. The amount of feedstock, and thereby the amount of adsorbent needed, determines the size of the column needed for the purification. A suitable column can be the commercially available FastLine™ columns from UpFront Chromatography A/S, Denmark, or as illustrated in EP 0 538 350 (UpFront Chromatography A/S).

Fluidisation or expansion of the high density particulate materials (absorbents) according to the invention inside a reactor gives the possibility to handle crude feedstock. In fluidisation/expansion the adsorbents are lifted up by an upward liquid flow of buffer or feedstock. The expanded volume between the fluidised adsorbents allows feedstock comprising insoluble impurities to pass through the reactor without clogging the system. Thus, adsorbent particles having a density larger than the fluid and moving downwards due to gravity may be kept in a free, fluid phase by an upward flow of fluid.

Purification of nucleic acid (such as DNA, e.g. plasmid DNA) using chargeable moieties such as DEAE, PEI and QAE is advantageous in that the interaction between the negatively charged phosphate groups in the DNA molecule and positively charged amino groups in DEAE, PEI and QAE facilitates the separation. Other positively charged ligands is believed to provide the same advantages.

As mentioned above, the present invention also provides a method for the isolation or purification of a bio-macromolecule, wherein said bio-macromolecule is adsorbed to a particulate material as defined above and in the claims. It should be understood that the particulate material preferably is present in fluidised form in a fluid bed column.

In a more specific embodiment, the invention relates to a method for the purification or isolation of bio-macromolecule, the method comprising the steps of (a) contacting a feedstock comprising one or more bio-macromolecules with a fluidised bed of a particulate material as defined above and in the claims;

(b) optionally washing the particulate material in order to separate impurities from the particulate material and the bio-macromolecule(s); and (c) eluting the bio-macromolecule(s) from the particulate material.

The adsorbent is fluidised/expanded in the column with a flow of equilibration buffer that corresponds to 10–500 cm/h and preferable 200–400 cm/h. The equilibration buffer may consists of 10–100 mM buffer (e.g. Tris, acetate, citrate, glysine, carbonate, phosphate) and typically have a pH value between 2.0–13.0 such as 4.0–8.0, and typically a NaCl concentration in the range between 0.0–0.5 M. Thus, preferably, the fluidised bed of the particulate material is washed with an equilibration buffer prior to contacting with the feedstock. The adsorbent is most conveniently equilibrated in the column and the equilibration buffer is preferably applied at least until the bed is stabilised.

After the stabilisation of the bed, the bio-macromolecule containing feedstock is applied to the fluid bed with a flow rate typically in the range of 100–500 cm/h.

Typically, a feedstock with bio-macromolecules is pre-treated before it is applied to the fluidised/expanded bed. The pre-treatment is, e.g., pH adjustment, lysis of host cells containing plasmid DNA, cell grinding, precipitation, mechanical removal of solid impurities, etc. Host cells are harvested and destroyed mechanically, e.g. by grinding, or chemically. Usually are cells destroyed by an alkaline lysis with NaOH and SDS. The lysis can be followed by a neutralisation often by addition of acetate to the solution. It can be convenient to remove a major part of the cell debris mechanically before applying the raw material to the column.

Generally, the concentration of the bio-macromolecule such as plasmid DNA in the feedstock is in the range of 0.1–3,000 µg/ml, such as in the range of 10–1,000 µg/ml. However, much higher concentrations may be relevant in some systems.

With respect to the preparation of the feedstock, it is preferred that the feedstock which comprises the bio-macromolecule(s) furthermore comprises a salt such as NaCl, KCl, $K_2HPO_4$ or $NaSO_4$ in a concentration of 0.0–2.0 M, preferably 0.0–1.0 M, in particular 0.0–0.5 M. Furthermore, the feedstock which comprises the bio-macromolecule(s) typically furthermore comprises a buffer whereby the pH is kept in the range of 2.0–13.0. The buffer may be any one suitable in combination with the bio-macromolecule in question, typically a e.g. Tris, acetate, citrate, glysine, carbonate, phosphate buffer in a concentration of 5–100 mM.

As a model system to illustrate the invention and to determine both static and dynamic binding capacities a solution containing calf thymus DNA has been used (see the examples). The concentration of calf thymus DNA was in the range of 18–2200 µg/ml in a 10 mM Tris buffer system at pH 8-0.

Another parameter of importance is the amount of particulate material (adsorbent) used to purify or isolate a certain amount of the bio-macromolecule. Typically, the ratio between the bio-macromolecule and the particulate material (adsorbent) is in the range of 0.1–10.0 mg bio-macromolecule/ml adsorbent.

The effect of NaCl on the binding efficiency can be tested by adding NaCl in varying concentrations in the range of 0.0–3.0 M to the calf thymus containing solution. In feedstock with dilute concentration of DNA it is normally necessary to add NaCl to the feedstock to suppress or prevent cross-linking of the adsorbent particles.

In the case where plasmid DNA is the bio-macromolecule of interest, sophisticated pH adjustments can be use in the pre-treatment process (or as an integral part of the adsorption process—see below) and will normally lead to denaturation of chromosomal DNA while plasmid DNA is reversibly renatured. The level of contaminants can be reduced. Another contaminant is RNA. The level of RNA can be reduced by a treatment of the feedstock with RNAse. In the same way can the level of protein contaminants be reduced by a treatment of proteolytic enzymes. Enzymatic treatment of the feedstock can be performed in various way, e.g. by adding the enzymes to the feedstock or by applying the feedstock to a fluidised/expanded bed where the enzymatic activity is immobilised onto the fluidised/expanded particles. Enzymatic treatment can also be performed on the eluate from the fluidised/expanded bed chromatographic step, e.g. if the resolution of plasmid DNA and RNA is low, the eluate can be treated with RNAse to reduce the level of that contaminant.

The feedstock is normally applied until a target molecule break through of 0–100%, preferable 0–50% and most preferable 0–10% is observed.

After adsorption, the particulate material having adsorbed thereto the bio-macromolecule is normally (but optionally) washed (step b) with an aqueous equilibration buffer including NaCl. The equilibration buffer may consists of 10 mM buffer (e.g. Tris, acetate or citrate) and have a pH value between 2.0–13.0 and a NaCl concentration in the range between 0.0–1.5 M, preferable 0.0–0.5 M.

If desirable, the particulate material having adsorbed thereto the bio-macromolecule is subsequently eluted with a NaCl gradient and/or NaOH buffer (0.001–1.0 M) or a buffer having a pH of 2.0–13.0 (such as e.g. Tris, acetate, citrate, glysine, carbonate, phosphate) or aqueous solutions of monosaccharides. The gradient typically goes from 0–3.0 M NaCl, more preferable 0–2.0 M NaCl and most preferable 0–1.0 M NaCl. Elution can take place in fluidised/expanded or packed bed, fluidised/expanded bed is preferred.

Particularly interesting bio-macromolecules to be isolated or purified by the present method are nucleic acids, in particular plasmid DNA.

Another interesting application of the materials according to the invention is the use as carriers for cells. As it has been illustrated in example 11, the materials are suitable for capture of cells (illustrated by yeast cells), and it is therefore contemplated that the materials also can be used as microcarriers for cells in, e.g., fermentation processes.

The high density and small particle size of the material may thus be beneficially exploited as carriers for living cells in stabilised expanded bed, turbulent fluid bed or batchwise fermentation systems. In this instance it will be a significant advantage that the material has a very high surface area due to the small particle size so that a maximum number of cells can attach per liter of material and at the same time have direct access to the nutrient medium. This is in strong contrast to a number of known carriers, which allow cells to attach inside large pores of a particulate material and thus become restricted with respect to the accessibility of nutrients. The small particle size of the material according to this invention combined with the high density allows a fast separation of the immobilised cells whenever this is wished during or at the end of the fermentation process.

Based on the ability to attract cells and bio-molecules, it is also envisaged that the materials can be used as microcarriers for living and dead cells as well as enzymes and other bio-catalysts in applications where the catalytic activity of the cells or enzymes and other bio-catalysts are utilised. As should be understood from the above, cells, enzymes or other bio-catalysts may be adsorbed to the particulate material either by pendant groups which are positively charged at pH 4.0 or pendant groups which are affinity ligands for bio-molecules. When affinity ligands for bio-molecules are used as pendant groups, it will be possible to discriminate between various types of cells, enzymes or other bio-catalysts based on the recognition between the ligand and the target in question.

In the case of immobilised enzymes or other bio-catalysts it may also be advantageous to utilise a covalent chemical coupling method known per se to attach the enzyme or other bio-catalyst to the material.

Thus, the present invention also relates to a particulate material (as defined herein) where each particle carries at least one, preferably a plurality of, cells, enzymes or other bio-catalysts.

FIGURE LEGENDS

FIG. 1. Light microscope photograph of particles having diameters in the range of 20–40 μm. The photograph illustrates the solid non-porous core material (stainless steel—dark) of the particles and the outer polymeric base matrix (agarose—translucent) (UFC PEI(20–40)).

Figure 2:
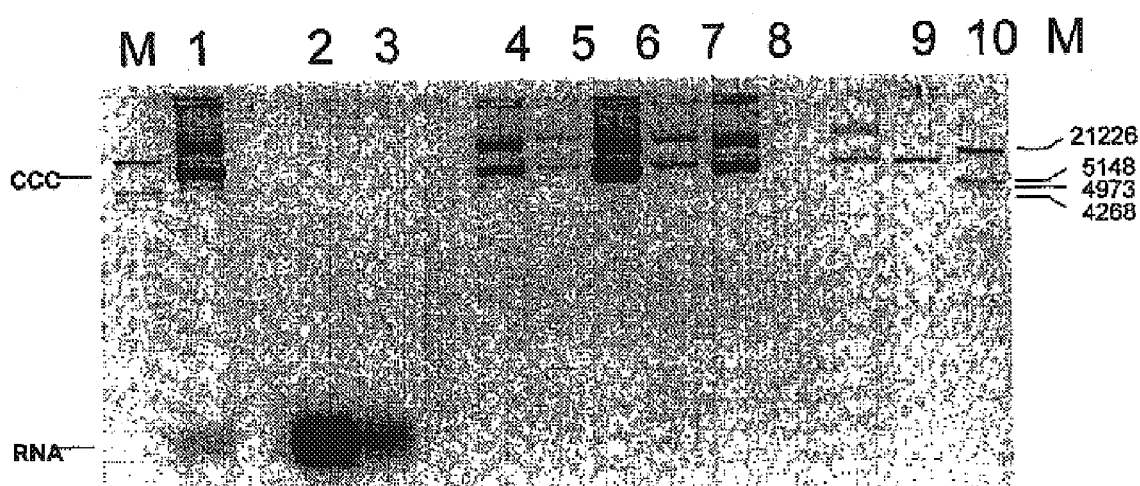

FIG. 2. Ethidium bromide-stained agarose gel of fractions from the expanded bed experiment described in example 8. Lane 1: alkaline lysate feedstock; lanes 2–3: RNA elution peak; lanes 4–8: DNA elution peak; lane 9: stripping peak; lane 10: plasmid DNA digested with BamHI; lane M: λ digested with HindIII and EcoRI. CCC: supercoiled plasmid DNA.

Figure 3:
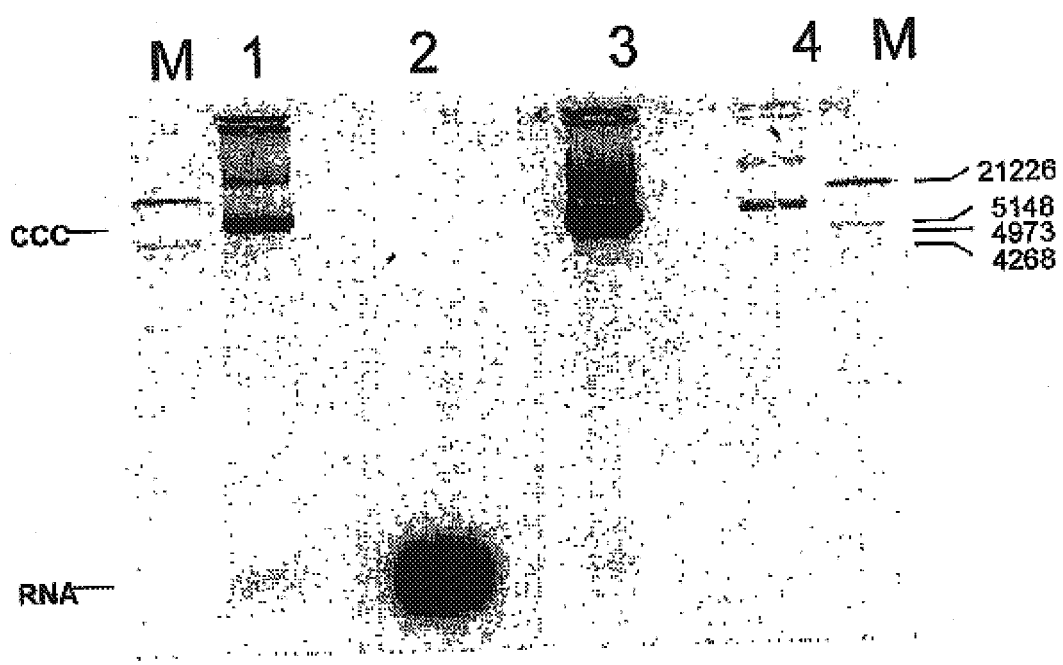

FIG. 3. Ethidium bromide-stained agarose gel of fractions from the expanded bed experiment described in example 9. Lane 1: alkaline lysate feedstock; lane 2: RNA elution peak; lane 3: DNA elution peak; lane 4: stripping peak; lane M: λ digested with HindIII and EcoRI. CCC: supercoiled plasmid DNA.

Figure 4:
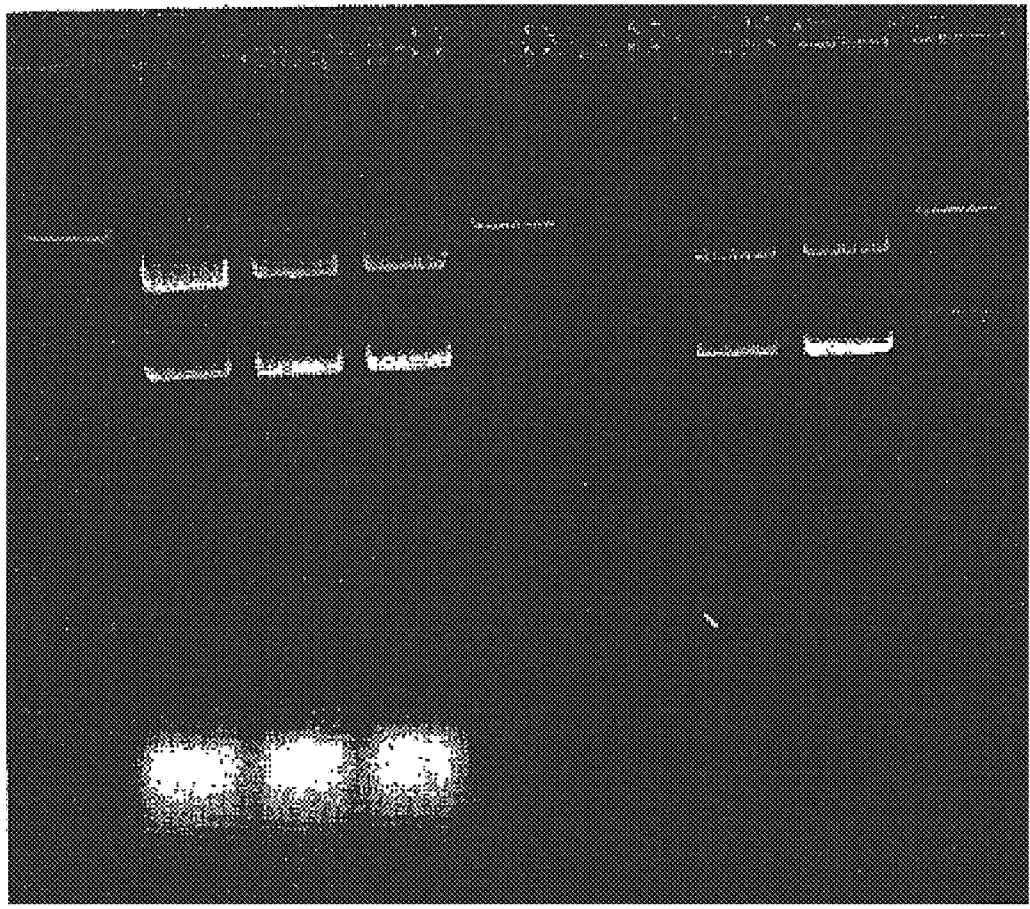

FIG. 4: Ethidium bromide-stained agarose gel of samples from experiment described in example 10. Lanes 1, 5 & 9: molecular weight marker, lanes 2–4: starting material containing pcDNA3, pV1 and pV2, respectively; lanes 6–8: eluted pcDNA3, pV1 and pV2, respectively.

Figure 5:
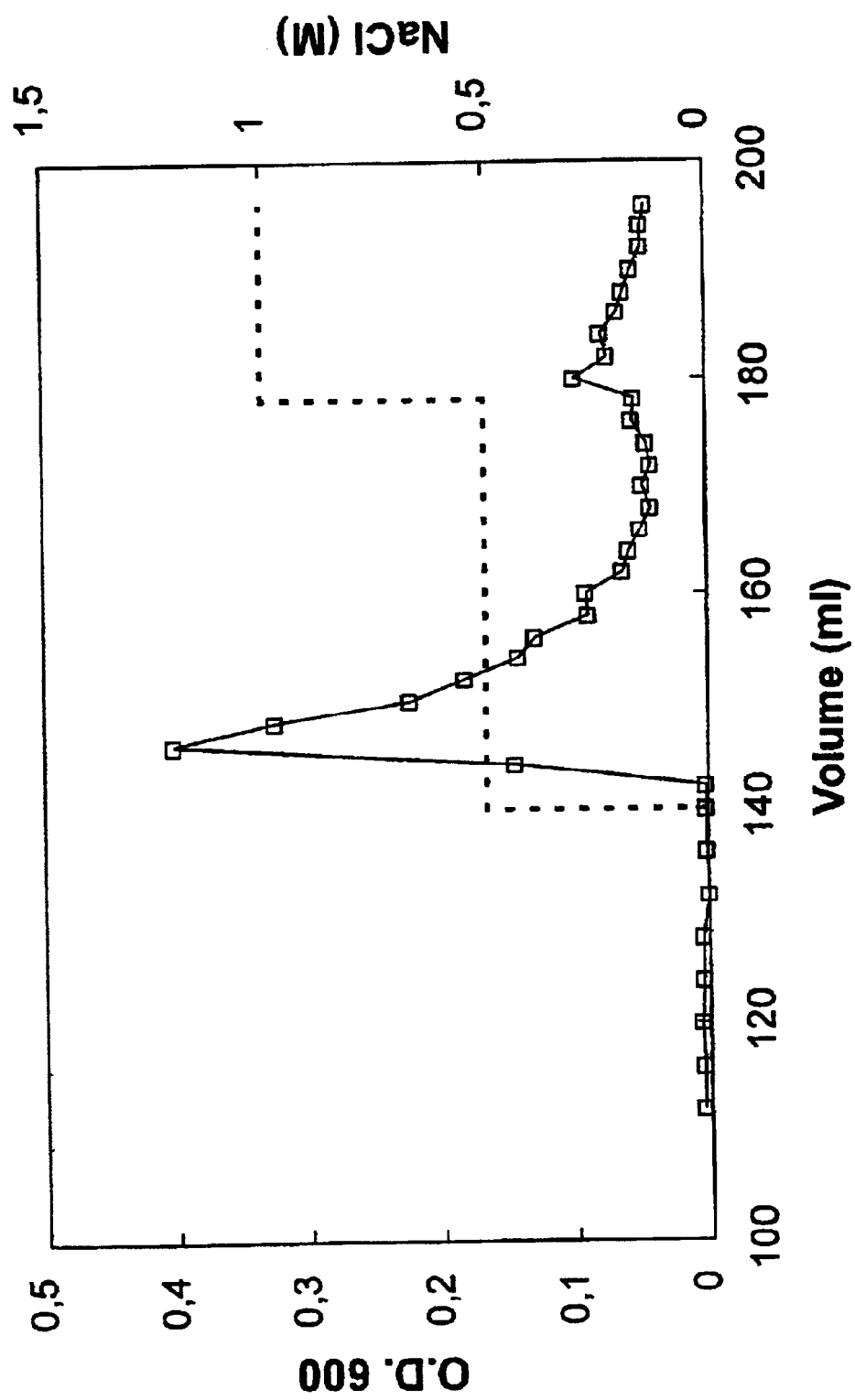

FIG. 5. Stepwise elution of yeast cells (from experiment described in example 12) using 50 mM Tris/HCl, pH 7.0 containing 0.5 M NaCl followed by the same buffer containing 1 M NaCl. Optical density at 600 nm (—), NaCl concentration (—).

EXAMPLES

Example 1

In this Example is the Preparation of a Calf Thymus DNA Solution Described. The Solution is Used in Example 4–7 for Model Binding Studies.

The solutions of calf thymus DNA used in example 4–7 for model studies are prepared in the following way:

100 mg calf thymus DNA (Sigma D 1501) is added to 50 ml 10 mM Tris/HCl pH 8.0. The solution is placed at room temperature over night. The solution is sonicated 30 minutes. The solution is then fractionated in aliquots of 2 ml. The aliquots are spinned at 13000 rpm for 5 minutes. The supernatants from the centrifuged aliquots are transferred to new tubes and stores at −20° C.

To determine the concentration of DNA the samples are measured at $A_{260\,nm}$ using Milli Q water as blank. $A_{260\,nm}=1$ corresponds to a DNA concentration of 50 μg/ml.

The majority of the DNA is between 3000 and 20,000 base pair as shown by gel electrophoresis.

Example 2

In this Example is the Derivatisation of the Adsorbents from UpFront Chromatography Used in Example 3–7

The term "UFC PEI (20–40)" refers to an adsorption media where the population size is within the range 20–40 μm, and PEI indicates that polyethyleneimine is used as the pendant group (ligand). The media is prepared from a population of adsorbents having a pellicular structure. They have a core material consisting of stainless steel beads (1-PSR-2, Anval, Sweden) (preferably only one bead per particle) sized in the range 22–44 μm. A layer of agarose surrounds the stainless steel core bead. The population is sieved to get a population size in the range of 20–40 μm. (An example of this particulate material is illustrated in FIG. 1.)

The term "UFC PEI (100–300)" refers to an adsorption media where the population size is with in the range 100–300. PEI indicates that polyethyleneimine is used as the pendant group (ligand). The media is prepared from a population of adsorbents having a pellicular structure. They have a core material consisting of glass beads (preferably only one bead per particle) from sized in the range 90–150 μm. A layer of agarose surrounds the glass bead core. The population is sieved to get a population size in the range of 100–300 μm (reference material).

The adsorbents are derivatised with PEI in the following way:

50 ml adsorbents (20–40 μm or 100–300 μm), 40 ml Milli Q water (75° C.), 6.3 ml epichlorohydrin and 5 ml 32.5% NaOH is mixed and the solution is shaken for 3.5 hours. Subsequent is the adsorbents washed with Milli-Q water. The washed epoxy activated adsorbents are coupled with PEI in the following way: 50 ml epoxy activated adsorbents plus 50 ml PEI solution 0.4 g/ml, pH 10.5 is shaken over night. Subsequent is the PEI derivatised adsorbents washed with Milli-Q water.

The ionic capacity of UFC PEI (20–40) is 0.14 mmol ($Cl^-$)/ml adsorbent.

The ionic capacity of UFC PEI (100–300) is 0.185 mmol ($Cl^-$)/ml adsorbent.

The term "UFC DEAE (20–40)" refers to an adsorption media where the population size is with in the range 20–40 μm as described above, except that DEAE is used as the pending group (ligand).

The term "UFC DEAE (100–300)" refers to an adsorption media where the population size is with in the range 100–300 as described above, except that DEAE is used as the pendant group (ligand).

The adsorbents are derivatised with DEAE in the following way:

50 ml adsorbents (20–40 μm or 100–300 μm), 40 ml Milli Q water (75° C.), 4.3 ml epichlorohydrin and 2.5 ml 32.5% NaOH is mixed and the solution is stirred for 3 hours. The solution is heated to 65° C. and 6.7 g NaOH and 6.1 g DEAE is added to the solution. The solution is stirred for 1 hour. Subsequent is 5.8 ml 32.5% NaOH and 6.1 g DEAE added 2 times with intervals of 1 hour. The heating is stopped and the solution is stirred over night.

The ionic capacity of UFC DEAE (20–40) is 0.05 mmol ($Cl^-$)/ml adsorbent.

The ionic capacity of UFC DEAE (100–300) is 0.08 mmol ($Cl^-$)/ml adsorbent.

In the batches produced in this example is the density of the 20–40μm adsorbents (stainless steel core) 3.7 g/ml, and the density of the 100–300μm adsorbents (glass core) 1.35.

Example 3

In this Example is Expansion Properties Described for UFC PEI (20–40).

Equipment: A Fastline™ 10 (UpFront Chromatography) and a column tube length of 30 cm, a Verder pump (Pericor) and a magnetic stirrer (Mini MR IKA Labortechnik).

Method: The settled bed height ($h_0$) is 5.0 cm. Milli-Q water is used to transfer the adsorbents into the column as well as the fluid used during the experiment. The column is levelled and the adjustable outlet is placed at the very top of the column. The pump and the magnetic stirrer are started. The speed of the magnetic stirrer is resulting in a local mixing zone in the bottom of the column that is less than 1 cm bed height. The flow rate is adjusted so that the bed expands about 3 times (approximately 4 ml/min). The bed is visually inspected to see if the bed is stable and there is no channelling. The expansion data are collected by measuring the expansion (h) that corresponds to a certain flow rate. The measurements are made at different flow rates. The degree of expansion is measured 15 minutes, where the bed height is stable after an adjustment of the flow rate.

| Flow rate (ml/min) | Flow rate (cm/h) | Degree of expansion (h/h₉) |
|---|---|---|
| 0 | 0 | 1.0 |
| 0.5 | 38 | 1.3 |
| 2.0 | 153 | 2.2 |
| 4.0 | 305 | 3.3 |
| 5.3 | 405 | 4.5 |
| 6.0 | 458 | 5.1 |

Comment/Conclusions:

Unfavourable bed expansion characteristics of typical small diameter beads is negated by the use of a very high density support (3.7 mg/ml). The degree of expansion is below 3.5, when the flow rate is in the range 60–300 cm/h, which is a typical range for running fluidised/expanded bed chromatography.

Example 4

In this Example is Static Binding Capacities of Calf Thymus DNA Described. Experiments to Describe the Adsorption Kinetic is Performed. Comparative Studies of Different Anion Exchangers are Performed.

Kinetic Studies:

6 identical incubations where performed:

400 μl 2.1 mg calf thymus DNA/ml, 10 mM Tris/HCl, pH 8.0 is added to 0.1 ml UFC PEI (20–40) adsorbent. This means that 8.4 mg DNA has been added per ml of adsorbent. The adsorbent is equilibrated in 10 mM Tris/HCl, pH 8.0. The incubations where stopped at different times; after 5, 10, 30, 60, 120 and 300 seconds. The solutions with DNA where analysed at $A_{260\ nm}$ and compared with the $A_{260\ nm}$ value of the solution before incubation.

| Incubation time (s) | Absorbance (260 nm) | % adsorbed | mg DNA adsorbed/ml adsorbent |
|---|---|---|---|
| 5 | 23.1 | 46 | 3.9 |
| 10 | 20.2 | 53 | 4.5 |
| 30 | 15.5 | 64 | 5.4 |
| 60 | 15.4 | 64 | 5.4 |
| 120 | 15.1 | 65 | 5.5 |
| 300 | 14.5 | 66 | 5.5 |

$A_{260nm}$ in the DNA solution before incubation was measured to be 42.8 which corresponds to 2.1 mg DNA/ml.

Comparative Studies of Binding Efficiencies of Different Anion Exchangers:

Static Experiment with DNA:

400 μl 2.1 mg calf thymus DNA/ml, 10 mM Tris/HCl, pH 8.0 is added to 0.1 ml adsorbent. This means that 8.4 mg DNA has been added per ml of adsorbent. The adsorbent is equilibrated in 10 mM Tris/HCl, pH 8.0. The incubations where stopped after 300 seconds. The solutions with DNA where analysed at $A_{260\ nm}$ and compared with the $A_{260\ nm}$ value of the solution before incubation. $A_{260\ nm}$ in the DNA solution before incubation was measured to be 42.8 corresponding to 2.1 mg DNA/ml.

Static Experiments with Bovine Serum Albumin (BSA):

4000 μl 2.2 mg BSA/ml, 10 mM Tris/HCl, pH 8.0 is added to 0.1 ml adsorbent. This means that 88 mg BSA has been added per ml of adsorbent. The adsorbent is equilibrated in 10 mM Tris/HCl, pH 8.0. The incubations where stopped after 300 seconds. The solutions with BSA where analysed at $A_{260\ nm}$ and compared with the $A_{260\ nm}$ value of the solution before incubation. $A_{260\ nm}$ in the BSA solution before incubation was measured to be 1.41.

| Adsorbent/ligand | Particle size[a] (μm) | Ionic capacity[a] (mmol (Cl⁻)/ml adsorbent) | Binding capacity (mg BSA/ml adsorbent) | Binding capacity[b] (mg DNA/ml adsorbent) |
|---|---|---|---|---|
| UFC PEI | 20–40 | 0.14 | 46[b] | 5.5 |
| UFC PEI | 100–300 | 0.18–0.20 | 90[c] | 0.6 |
| UFC DEAE | 20–40 | 0.05 | 22[b] | 2.7 |
| UFC DEAE | 100–300 | 0.05–0.10 | 70[c] | 0.3 |
| Q HyperD (M) | Av. 50 | 0.14–0.18 | 100[c] | 1.6 |
| DEAE Sepharose FF | 45–165 | 0.11–0.16 | 110[c] | 0.2 |
| Q Sepharose FF | 45–165 | 0.18–0.25 | 120[c] | 0.5 |
| STREAMLINE DEAE | 100–300 | 0.13–0.21 | 40–55[c] | 0.2 |

[a]manufactures figures
[b]determined in static binding experiments
[c]manufacturer's figures for dynamic capacities Comments/Conclusions:

In comparative static binding tests with high molecular weight calf thymus DNA, the support according to the invention, derivatised with DEAE and PEI in particular, possesses DNA binding capacities significantly higher than those of commercially available anion exchange media. Not surprisingly, these improvements where achieved at the expense of reduced capacities for protein adsorption given the thin layer of agarose on the prototype support.

The kinetics of equilibrium adsorption of DNA to these supports were extremely fast (1–30 seconds).

Example 5

In this Example are Static Binding Experiments on UFC PEI (20–40) Performed with a Solution of Calf Thymus DNA having a Concentration of DNA (about 20 μg/ml) that is about the Concentration of Plasmid DNA in Fermentation Liquors. The Experiments are Performed with Varying Concentrations of NaCl.

The adsorbent is equilibrated in 10 mM Tris/HCl, pH 8.0.

The calf thymus DNA solution is made from a stock solution (2.0 mg/ml, 10 mM Tris, pH 8.0) by dilution with a 10 mM Tris/HCl, pH 8.0 buffer. NaCl is added to fractions of the diluted solutions to get varying concentrations NaCl (see incubation conditions):

Incubation Conditions (for 10 Minutes):

0.1 ml UFC PEI (20–40)+4.0 ml 20 μg DNA/ml, 10 mM Tris/HCl, pH 8.0

0.1 ml UFC PEI (20–40)+4.0 ml 20 μg DNA/ml, 25 mM NaCl, 10 mM Tris/HCl, pH 8.0

0.1 ml UFC PEI (20–40)+4.0 ml 20 μg DNA/ml, 75 mM NaCl, 10 mM Tris/HCl, pH 8.0

0.1 ml UFC PEI (20–40)+4.0 ml 20 μg DNA/ml, 0.2 M NaCl, 10 mM Tris/HCl, pH 8.0

0.1 ml UFC PEI (20–40)+4.0 ml 20 μg DNA/ml, 0.5 M NaCl, 10 mM Tris/HCl, pH 8.0

0.1 ml UFC PEI (20–40)+4.0 ml 20 μg DNA/ml, 0.75 M NaCl, 10 mM Tris/HCl, pH 8.0

0.1 ml UFC PEI (20–40)+4.0 ml 20 μg DNA/ml, 1.0 M NaCl, 10 mM Tris/HCl, pH 8.0

0.1 ml UFC PEI (20–40)+4.0 ml 20 μg DNA/ml, 1.5 M NaCl, 10 mM Tris/HCl, pH 8.0

0.1 ml UFC PEI (20–40)+4.0 ml 20 µg DNA/ml, 2.1 M NaCl, 10 mM Tris/HCl, pH 8.0

0.1 ml UFC PEI (20–40)+4.0 ml 20 µg DNA/ml, 3.1M NaCl, 10 mM Tris/HCl, pH 8.0

0.8 mg DNA is incubated per ml adsorbent. Absorbance is detected after 10 minutes incubation time at 260 nm and compared to the absorbance in the DNA solutions before incubation. The absorbents where visually inspected after incubation to see if there where cross-linking or flocculation of the single beads.

| NaCl concentration (mM) | Capacity (mg/ml adsorbent) | Cross-linking (yes/no) |
| --- | --- | --- |
| 0 | 0.6 | Yes |
| 25 | 0.7 | Yes |
| 75 | 0.7 | Yes |
| 200 | 0.6 | Yes |
| 500 | 0.7 | No |
| 750 | 0.05 | No |
| 1000 | 0 | No |
| 1500 | 0 | No |
| 2100 | 0 | No |
| 3100 | 0 | No |

Determination of the DNA Binding Capacity of UFC PEI (20–40) from a 20 µg DNA/ml Solution with 0.5 M NaCl Incubation conditions (for 60 min):

0.1 ml UFC PEI (20–40)+10 ml 20 µg DNA/ml, 0.5 M NaCl, 10 mM Tris/HCl, pH 8.0

0.1 ml UFC PEI (20–40)+20 ml 20 µg DNA/ml, 0.5 M NaCl, 10 mM Tris/HCl, pH 8.0

0.1 ml UFC PEI (20–40)+30 ml 20 µg DNA/ml, 0.5 M NaCl, 10 mM Tris/HCl, pH 8.0

0.1 ml UFC PEI (20–40)+40 ml 20 µg DNA/ml, 0.5 M NaCl, 10 mM Tris/HCl, pH 8.0

The absorbance at 260 nm is measured in the incubated solution after 60 minutes, and compared to the absorbance at 260 nm in the DNA solution before incubation.

| DNA solution (ml) | DNA added/ml adsorbent | A (260 nm) after incubation | % adsorbed | Adsorption efficiency (mg DNA/ml adsorbent) |
| --- | --- | --- | --- | --- |
| 10 | 2.0 | 0.034 | 92 | 1.94 |
| 20 | 4.0 | 0.089 | 79 | 3.16 |
| 30 | 6.0 | 0.140 | 67 | 4.02 |
| 40 | 8.0 | 0.224 | 49 | 3.76 |

The absorbance at 260 nm is measured in the solution before the incubations: 0.40 which corresponds to a concentration of 20 µg/ml.

Comments/Conclusions:

In batch adsorption studies at low DNA concentrations (20 µg/ml) we have observed extensive gelling of the prototype PEI-based anion exchanger whereas this effect was not seen at much higher DNA concentrations, e.g. 2 mg/ml. The addition of NaCl to a molarity of about 0.5 prevented this from occurring without reducing binding capacity. However, when the NaCl concentration was raised above 0.5 M a sharp decrease in DNA adsorption was observed.

In static binding tests with DNA concentration of 20 µg/ml and 0.5 M NaCl the capacity of the adsorbent is about 4 mg/ml adsorbent.

Example 6

In this Example is a Breakthrough Curves Made for UFC PEI (20–40) in Fluidised/Expanded Bed Adsorption with a DNA Solution of about 20 µg/ml DNA, 0.5 M NaCl, 10 mM Tris/HCl, pH 8.0 Described.

Equipment: Pump, column 1 cm in diameter, magnetic stirrer

Method: Adsorbent: UFC PEI (20–40). Equilibrated adsorbent is filled into the column already containing a magnetic bar. The adsorbent is equilibrated with 0.5 M NaCl, 10 mM Tris/HCl, pH 8.0. The settled bed height is 4 cm corresponding to 3.2 ml adsorbent. The adsorbent is expanded to 12 cm by a flow rate of 300 cm/min equilibration buffer and the magnetic stirrer is started with a speed that not will result in a mixing zone in the bottom of the column that is more than 1 cm. The adjustable outlet of the column is placed approximately 1 cm above the expanded bed.

The pump inlet is shifted to a DNA solution 18.0 µg/ml DNA, 0.5 M NaCl, 10 mM Tris/HCl, pH 8.0. The run through of the column is collected in 50 ml fractions, which are analysed by $A_{260\ nm}$, and the concentration of DNA, C, is calculated. The absorbance at 260 nm of the DNA solution before it is applied to the column is 0.36 corresponding to a DNA concentration, $C_0$, of 18.0 µg/ml.

| Fraction | Total volume of DNA solution applied (ml) | Absorbance in run through | % DNA in run through ($C/C_o$) |
| --- | --- | --- | --- |
| 1 | 50 | 0.000 | 0 |
| 2 | 100 | 0.000 | 0 |
| 3 | 150 | 0.000 | 0 |
| 4 | 200 | 0.000 | 0 |
| 5 | 250 | 0.000 | 0 |
| 6 | 300 | 0.000 | 0 |
| 7 | 350 | 0.000 | 0 |
| 8 | 400 | 0.000 | 0 |
| 9 | 450 | 0.000 | 0 |
| 10 | 500 | 0.000 | 0 |
| 11 | 550 | 0.000 | 0 |
| 12 | 600 | 0.001 | 0.2 |
| 13 | 650 | 0.001 | 0.2 |
| 14 | 700 | 0.002 | 0.5 |
| 15 | 750 | 0.003 | 0.8 |
| 16 | 800 | 0.008 | 2.0 |
| 17 | 850 | 0.011 | 3.0 |
| 18 | 900 | 0.018 | 5.0 |
| 19 | 950 | 0.021 | 6.0 |
| 20 | 1000 | 0.033 | 10.0 |
| 21 | 1050 | 0.053 | 15.0 |
| 22 | 1100 | 0.078 | 23.0 |
| 23 | 1150 | 0.103 | 30.0 |
| 24 | 1200 | 0.128 | 37.0 |
| 25 | 1250 | 0.133 | 39.0 |

Comments/Conclusion:

There is 10% breakthrough after 1000 ml is applied. That corresponds to 18 mg DNA applied. Thereby is the dynamic capacity 5.6 mg/ml adsorbent at 10% break through.

Example 7

In this Example is a Breakthrough Curves Made for UFC PEI (20–40) in Fluidised/Expanded Bed Adsorption with a DNA Solution of about 20 µg/ml DNA, 10 mM Tris/HCl, pH 8.0 Described.

Equipment: Pump, column 1 cm in diameter, magnetic stirrer

Method: Adsorbent: UFC PEI (20–40). Equilibrated adsorbent is filled into the column already containing a magnetic bar. The adsorbent is equilibrated with 10 mM Tris/HCl, pH 8.0 The settled bed height is 4 cm corresponding to 3.2 ml adsorbent. The adsorbent is expanded to 12 cm by a flow rate of 300 cm/min equilibration buffer and the magnetic stirrer is started with a speed that does not result in a local mixing zone in the bottom of the column that is more than 1 cm. The adjustable outlet of the column is placed approximately 1 cm above the expanded bed. The pump inlet is shifted to the DNA solution 20.0 µg/ml DNA, 10 mM Tris/HCl, pH 8.0. The run through of the column is collected in 50 ml fractions, which are analysed by A 260 nm. The absorbance at 260 nm of the DNA solution before it is applied to the column is 0.39 corresponding to a DNA concentration of 19.5 µg/ml.

| Fraction | Total volume of DNA solution applied (ml) | Absorbance of run through at 260 nm | % DNA in run through (C/Co) |
| --- | --- | --- | --- |
| 1 | 50 | 0.000 | 0.0 |
| 2 | 100 | 0.000 | 0.0 |
| 3 | 150 | 0.000 | 0.0 |
| 4 | 200 | 0.000 | 0.0 |
| 5 | 250 | 0.000 | 0.0 |
| 6 | 300 | 0.000 | 0.0 |
| 7 | 350 | 0.000 | 0.0 |
| 8 | 400 | 0.000 | 0.0 |
| 9 | 450 | 0.000 | 0.0 |
| 10 | 500 | 0.000 | 0.0 |
| 11 | 550 | 0.000 | 0.0 |
| 12 | 600 | 0.000 | 0.0 |
| 13 | 650 | 0.000 | 0.0 |
| 14 | 700 | 0.034 | 9.0 |

Comments/Conclusion

In the absence of NaCl breakthrough occurred after ~4 mg of DNA had been applied per ml of adsorbent. At this point severe gelation was observed and the media, in form of a plug, expanded out of the column. The experiment had to be stopped.

Example 8

Separation of RNA and Plasmid DNA from Neutralised *Escherichia coli* Lysates Using UFC DEAE (20–40 µm) Adsorbent and Continuous Linear Ionic Strength Gradient Elution.

The feedstock used in this example is prepared as follows: an 8.5 kb runaway plasmid (pOU61) is transformed into *Escherichia coli* DH5-alpha cells and propagated by fermentation. Following fermentation cells are harvested by centrifugation, resuspended in an RNase (100 µg/ml) containing buffer and lysed under alkaline conditions in the presence of sodium dodecyl sulphate. The alkaline lysate is then neutralised with 3 M potassium acetate, pH 5.5 and the plasmid containing liquor drained from underneath a floating floc of denatured proteins and chromosomal DNA. The final DNA, RNA and protein contents of the neutralised lysate are 53 µg/mL, 680 µg/mL and 360 µg/ml respectively.

Equipment: FastLine™ 10 column, (1 cm in diameter and 30 cm in height), magnetic stirrer, GradiFrac™ System including a HiLoad Pump P-50, a fraction collector and a REC102 chart recorder.

Method: Adsorbent: UFC DEAE (20–40 µm). The adsorbent is added to the column, which already contains a magnetic stirring bar. The adsorbent is washed with 0.1 M NaOH for 1 hour at a linear flow rate of 153 cm/h. The bed is allowed to settle and is left in 0.1 M NaOH overnight. The adsorbent is then equilibrated with 0.8 M potassium acetate, 10 mM EDTA, pH 5.5. The settled bed height is 5.5 cm corresponding to 4.3 ml adsorbent. The adsorbent is expanded to a height of 11.4 cm with equilibration buffer at a linear now rate of 153 cm/h and the magnetic stirrer is started with a speed of 750 rpm, which is kept constant throughout the experiment. The adjustable outlet of the column is placed approximately 1 cm above the expanded bed. Following equilibration for 2 hours, 40 ml of neutralised *E. coli* lysate is pumped through the column at a linear flow rate of 153 cm/h. The adsorbent is then washed with equilibration buffer for 26 min followed by 25 mM potassium acetate, 10 mM EDTA, pH 5.5 until the on-line absorbance signal reaches the base line on the chart recorder. Bound RNA is eluted from the adsorbent in a stepwise manner using 0.66 M NaCl (in 25 mM potassium acetate, 10 mM EDTA, pH 5.5). Plasmid DNA is then eluted by applying a linear ionic strength gradient starting from 0.66 M NaCl (in 25 mM potassium acetate, 10 mM EDTA, pH 5.5) and finishing at 1 M NaCl (in 25 mM potassium acetate, 10 mM EDTA, pH 5.5) in a period of 2 hours. Following elution, material still bound to the adsorbent is removed with a stripping buffer (2 M NaCl, 0.2 M NaOH). The liquid exiting the column is collected in 4 ml fractions and the compositions of each fraction are analysed by electrophoresis and assays for protein, RNA and DNA.

Comments/Conclusion:

Complete separation of RNA from DNA is achieved using the conditions described above (FIG. 2), and >95% of the protein is collected during sample loading. Nearly 80% of the supercoiled plasmid DNA applied to the expanded bed of UFC DEAE (20–40 µm) adsorbent is eluted in the applied linear gradient, and is completely free of RNA and protein.

Example 9

Separation of RNA and Plasmid DNA from Neutralised *Escherichia coli* Lysates Using UFC DEAE (20–40 µm) Adsorbent and Stepwise Ionic Strength Gradient Elution.

The feedstock used in this example is prepared as follows: an 8.5 kb runaway plasmid (pOU61) is transformed into *Escherichia coli* DH5-alpha cells and propagated by fermentation. Following fermentation cells are harvested by centrifugation, resuspended in an RNase (100 µg/ml) containing buffer and lysed under alkaline conditions in the presence of sodium dodecyl sulphate. The alkaline lysate is then neutralised with 3 M potassium acetate, pH 5.5 and the plasmid containing liquor drained from underneath a floating floc of denatured proteins and chromosomal DNA. The final DNA, RNA and protein contents of the neutralised lysate are 53 µg/mL, 650 µg/mL and 320 µg/mL respectively.

Equipment: FastLine™ 10 column, (1 cm in diameter and 30 cm in height), magnetic stirrer, GradiFrac™ System including a HiLoad Pump P-50, a fraction collector and a REC102 chart recorder.

Method: Adsorbent: UFC DEAE (20–40 µm). The adsorbent is added to the column, which already contains a magnetic stirring bar. The adsorbent is washed with 0.1 M NaOH for 1 hour at a linear flow rate of 153 cm/h. The bed is allowed to settle and is left in 0.1 M NaOH overnight. The adsorbent is then equilibrated with 0.8 M potassium acetate, 10 mM EDTA, pH 5.5. The settled bed height is 5.4 cm corresponding to 4.2 ml adsorbent. The adsorbent is expanded to a height of 11.3 cm with equilibration buffer at a linear flow rate of 153 cm/h and the magnetic stirrer is started with a speed of 750 rpm which is kept constant throughout the experiment. The adjustable outlet of the column is placed approximately 1 cm above the expanded bed. Following equilibration for 2 hours, 40 ml of neutralised *Escherichia coli* lysate is pumped through the column at a linear flow rate of 153 cm/h. The adsorbent is then washed with equilibration buffer for 25 min followed by 25 mM potassium acetate, 10 mM EDTA, pH 5.5 until the on-line absorbance signal reaches the base line on the chart recorder. Bound RNA is eluted from the adsorbent using 0.66 M NaCl (in 25 mM potassium acetate, 10 mM EDTA, pH 5.5). Plasmid DNA is then eluted using 1 M NaCl (in 25 mM potassium acetate, 10 mM EDTA, pH 5.5). Following elution, material still bound to the adsorbent is removed with a stripping buffer (2 M NaCl, 0.2 M NaOH). The liquid exiting the column is collected in 4 ml fractions and the compositions of each fraction are analysed by electrophoresis and assays for protein, RNA and DNA.

Comments/conclusion: By applying a simple stepwise ionic strength gradient elution, separation of RNA from DNA is achieved (FIG. 3). Recovery of supercoiled plasmid DNA is >75%.

Example 10

Affinity Capture of Plasmid DNA from *Escherichia coli* Lysates Using UFC (20–40 μm) Adsorbent Derivatised with an Affinity Ligand.

A fragment of DNA containing the sequence $d(GAA)_{17} \cdot d(TTC)_{17}$ is inserted into a commercial expression vector (pcDNA3, Invitrogen, USA) in the Bst1 107 I restriction site to generate plasmid pV1 or in Bst1 107 I restriction site and in the Bgl II restriction site to generate plasmid pV2. Each plasmid is transformed into DH5-alpha *E. coli* cells and propagated by fermentation.

Following the fermentation cells are harvested and lysed under alkaline conditions in the presence of sodium dodecyl sulphate. The lysate is neutralised and adjusted to binding conditions (2 M NaCl, 0.2 M Acetate buffer; pH 4.5) and to a final DNA content of 8±1 μg/ml.

Method; Adsorbent: UFC $(CTT)_7$ affinity (20–40 μm). Avidin-coated UFC (20–40 μm) adsorbent is derivatised with 1 nmol of biotin-labelled $(CTT)_7$ oligonucleotide per ml of matrix to produce the affinity adsorbent.

The affinity adsorbent is washed once with 0.15 M NaCl, 20 mM sodium phosphate buffer, pH 7.5 and then equilibrated in 2 M NaCl, 0.2 M potassium acetate buffer, pH 4.5. The adsorbent is then mixed gently by tumbling end-over-end with bacterial lysate containing either pV0, pV1 or pV2 at a ratio of 160±20 μg of DNA per ml of affinity adsorbent. After 20 hours the adsorbent is washed twice with 0.5 volume of 2 M NaCl, 0.2 M potassium acetate buffer, pH 4.5 and then elution of the plasmid is achieved by incubation for 30 minutes in 0.5 volume of elution buffer (1 M Tris, 1 mM EDTA, pH 10.6). The plasmid-containing supernatant is separated and analysed by agarose gel electrophoresis followed by ethidium bromide staining and visualisation under UV light (FIG. 4)

Comments/conclusion: Only plasmids carrying the specific target sequence are captured from the plasmid-containing bacterial lysate by the UFC (20–40 μm) affinity adsorbent (FIG. 4).

Example 11

Yeast Cell Capture from Buffer Using UFC DEAE (20–40 μm) Adsorbent.

Equipment: FastLine™ 10 column (1 cm in diameter and 30 cm in height), Verder CD70 pump, magnetic stirrer, spectrophotometer.

Method: Adsorbent: UFC DEAE (20–40 μm). The adsorbent is added to the column, which already contains a magnetic stirring bar. The adsorbent is washed and equilibrated with 50 mM Tris/HCl pH 7.0 buffer for 2 hours at a linear flow velocity of 153 cm/h. The settled bed height is 4 cm corresponding to 3.15 ml adsorbent. The adsorbent is expanded to a height of 9.5 cm with equilibration buffer at a linear flow rate of 153 cm/h and the magnetic stirrer is started with a speed of 750 rpm, which is kept constant throughout the experiment. A linear flow velocity of 153 cm/h is used for all solutions that are passed through the column. The adjustable outlet of the column is placed approximately 1 cm above the expanded bed. Commercial baker's yeast is added to equilibration buffer to give an optical density at 600 nm (O.D. 600) of 1.42, equivalent to 0.39 g/l dry wt. The cell-containing solution is pumped to the column and the liquid exiting the column is collected in 2 ml fractions and analysed for yeast cell content by monitoring the optical density at 600 nm in a spectrophotometer.

Comments/Conclusion:

No breakthrough of yeast cells is detected when 760 ml of buffer containing cells (0.30 g dry wt) was passed through the column. The dynamic breakthrough capacity of the UFC (20–40 μm) DEAE adsorbent for yeast cells under these conditions is therefore greater than 0.095 g dry wt. cells per ml of adsorbent.

Example 12

Yeast Cell Capture from Fermentation Medium Using UFC DEAE (20–40 μm) Adsorbent and Step Ionic Strength Gradient Elution.

Equipment: FastLine™ 10 column (1 cm in diameter and 30 cm in height), Verder CD70 pump, magnetic stirrer, spectrophotometer.

Method: Adsorbent: UFC DEAE (20–40 μm). The adsorbent is added to the column, which already contains a magnetic stirring bar. The adsorbent is washed and equilibrated with 50 mM Tris/HCl pH 7.0 buffer for 2 hours at a linear flow velocity of 153 cm/h. The settled bed height is 3.9 cm corresponding to 3.05 ml adsorbent. The adsorbent is expanded to a height of 9.5 cm with equilibration buffer at a linear flow rate of 153 cm/h and the magnetic stirrer is started with a speed of 750 rpm, which is kept constant throughout the experiment. A linear flow velocity of 153 cm/h is used for all solutions which are passed through the column. The adjustable outlet of the column is placed approximately 1 cm above the expanded bed. Sufficient commercial baker's yeast to give a dry weight (dry wt.) concentration of 0.52 g/l corresponding to an optical density at 600 nm (O.D. 600) of 1.82 is added to a defined fermentation medium containing mineral salts, glucose (10 g/l) and trace metals (Verduyn et al., 1992, *Yeast*, 8: 501–517). The yeast-containing medium (84 ml) is pumped through the column, the adsorbent is then washed with equilibration buffer during which the O.D. 600 reaches the baseline. Yeast cells are eluted from the adsorbent in a stepwise manner using equilibration buffer containing 0.5 M NaCl and in a subsequent elution step, with addition of equilibration buffer containing 1 M NaCl. The liquid exiting the column is collected in 2 ml fractions.

Comments/Conclusion:

Ten-percent breakthrough occurs after 10 ml of cell suspension is applied. The dynamic binding capacity determined at 10% breakthrough is 1.7 mg dry wt. cells per ml adsorbent. Application of buffer containing 0.5 M and 1 M NaCl results in elution of yeast cells (FIG. 5) from the UFC (20–40 μm) adsorbent bed.

What is claimed is:

1. A particulate material having a density of at least 2.5 g/ml, comprised of particles having an average diameter of 5–75 μm, wherein said particles of the particulate material are essentially constructed of a polymeric base matrix and a non-porous core material, said core material having a density of at least 3.0 g/ml, and said polymeric base matrix comprising either chargeable pendant groups or affinity ligands for a bio-molecule.

2. The material according to claim 1, wherein the average diameter of the particles is in the range of 10–60 μm.

3. The material according to claim 1, wherein at least 95% of the particles have a diameter in the range of 5–80 μm.

4. The material according to claim 1, wherein the density of the particles is at least 3.0 g/ml.

5. The material according to claim 1, wherein the pendant groups comprise chargeable moieties selected from polyethyleneimine, modified polyethyleneimine, poly (ethyleneimine/oxyethylene), quaternary aminoethyl(QAE) and diethylaminoethyl, (DEAE).

6. The material according to claim 5, wherein the pendant groups are polyethyleneimine chains having an weight average molecular weight of at least 10,000 Daltons.

7. The material according to claim 5, wherein the pendant groups form a tentacular structure on the surface of the particle.

8. The material according to claim 1, wherein the core material has a density in the range of 6.0–12.0 g/ml.

9. The material according to claim 1, wherein the core material of at least 95% of the particles is a steel bead having a diameter in the range of 2–40 μm.

10. The material according to claim 1, wherein at least 95% of the particles comprises one non-porous core material bead having a diameter which is a least 0.70 of the diameter of the particle.

11. The material according to claim 1, wherein the core material comprises more than one bead.

12. The material according to claim 1, wherein the core material constitutes 10–99% of the volume of the particles, and the polymer base matrix constitutes 1–90% of the volume of the particle.

13. The material according to claim 1, wherein the polymeric base matrix is selected from polysaccharides.

14. The material according to claim 1, wherein at least 95% of the particles are substantially spherical.

15. The material according to claim 1, wherein the chargeable pendent groups are positively charged at pH 4.0.

16. A method for the isolation or purification of a bio-macromolecule, wherein said bio-macromolecule is adsorbed to a particulate material as defined in claim 1.

17. The material according to claim 16, wherein the particulate material is present in fluidized form in a fluid bed column.

18. A method for the purification of bio-macromolecule (s); the method comprising the steps of
  (a) contacting a feedstock comprising one or more bio-macromolecules with a fluidized bed of a particulate material as defined in claim 1;
  (b) eluting the bio-macromolecule(s) from the particulate material.

19. The method according to claim 18, wherein the fluidized bed of the particulate material is washed with an equilibration buffer prior to contacting with the feedstock.

20. The method according to claim 18, wherein the concentration of the bio-macromolecule in the feedstock is in the range of 0.1–3,000 μm/ml.

21. The method according to claim 20, wherein the feedstock comprising the bio-molecules(s) further comprises NaCl in a concentration of 0.01–2.0M.

22. The method according to claim 20, wherein the feedstock comprising the bio-macromolecule(s) further comprises a buffer whereby the pH is in the range of 4.0–8.0.

23. The method according to claim 18, wherein the ratio between the bio-macromolecule and the particulate material is in the range of 0.1–7.0 mg bio-macromolecule/ml particulate material.

24. The method according to claim 18, wherein the bio-macromolecule has a molecular weight of at least 20,000 Daltons.

25. The method according to claim 19, wherein the equilibration buffer includes NaCl.

26. The method according to claim 18, wherein a NaCl gradient and/or NaOH buffer is used to elute the bio-macromolecule(s) from the particulate material in step (b).

27. The method according to claim 18, wherein the fluidized bed is a stabilized expanded bed without significant back-mixing.

28. The method according to claim 18, wherein the particulate material has a density of in the range of 3.2–5.0 g/ml, and comprises particles having an average diameter of 15–45 μm, and the particles are essentially constructed of a polysaccharide base matrix and a core material, said core material having a density in the range of 6.0–12.0 g/m$^3$, said polysaccharide base matrix including pendant groups selected from polyethyleneimine chains, modified polyethyleneimine chains and poly(ethyleneimine/oxyethylene) chains, said pendant groups forming a tentacular structure on the surface of the particle.

29. The method according to claim 18, wherein the bio-macromolecule is a nucleic acid.

30. The method according to claim 29, wherein the nucleic acid is plasmid DNA.

31. The method according to claim 18, wherein the particulate material is washed to separate impurities from the particulate material and the bio-macromolecule(s) after the particulate material is contacted with the feedstock in step (a).

32. A particulate material having a density of in the range of 3.2–5.0 g/ml, comprised of particles having an average diameter of 15–45 μm, and the particles of the particulate material are essentially constructed of a polysaccharide base matrix and a core material, said core material having a density in the range of 6.0–12.0 g/m$^3$, said polysaccharide base matrix including pendant groups selected from polyethyleneimine chains, modified polyethyleneimine chains and poly(ethyleneimine/oxyethylene) chains, said pendant groups forming a tentacular structure on the surface of the particle.

* * * * *